United States Patent
Kim et al.

(10) Patent No.: US 11,045,559 B2
(45) Date of Patent: Jun. 29, 2021

(54) REACTIVE FLUOROGENIC COMPOUND AND NANOCOMPOSITE FOR SENSING HYDROGEN SULFIDE COMPRISING THE SAME

(71) Applicant: KOREA INSTITUTE OF SCIENCE AND TECHNOLOGY, Seoul (KR)

(72) Inventors: Sehoon Kim, Seoul (KR); Myung Kim, Seoul (KR); Young Hun Seo, Seoul (KR); Jungyun Heo, Seoul (KR); Youngsun Kim, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 27 days.

(21) Appl. No.: 16/034,898

(22) Filed: Jul. 13, 2018

(65) Prior Publication Data
US 2019/0076554 A1    Mar. 14, 2019

(30) Foreign Application Priority Data

Sep. 8, 2017    (KR) .................. 10-2017-0115431

(51) Int. Cl.
*A61K 49/00* (2006.01)
*G01N 21/77* (2006.01)
*G01N 21/64* (2006.01)
*B82Y 5/00* (2011.01)

(52) U.S. Cl.
CPC ...... *A61K 49/0028* (2013.01); *A61K 49/0076* (2013.01); *G01N 21/6428* (2013.01); *G01N 21/77* (2013.01); *B82Y 5/00* (2013.01); *G01N 2021/7786* (2013.01)

(58) Field of Classification Search
None
See application file for complete search history.

(56) References Cited

U.S. PATENT DOCUMENTS

2013/0323178 A1* 12/2013 Yamauchi ............ A61K 49/226
424/9.5

OTHER PUBLICATIONS

Calderon-Colon, X., et al., "Synthesis of sub-10 nm solid lipid nanoparticles for topical and biomarker detection applications", J. Nanopart. Res., pp. 2251-2261 (Year: 2014).*
Karn-orachai, K., et al., "Surfactant effect on the physicochemical characteristics of γ-oryanol-containing solid lipid nanoparticles", Colloids and Surfaces A, pp. 118-128 (Year: 2016).*
Saha, T., et al., "Performance comparison of two cascade reaction models in fluorescence off-on detection of hydrogen sulfide", RSC Adv., pp. 1438-1446 (Year: 2015).*
Jiang, Y., et al., "A ratiometric fluorescent probe for hydrogen sulfide imaging in living cells", Talanta, pp. 122-126 (Year: 2014).*
Nikoleis, D.P., et al., "Control of ion transport across bilayer lipid membranes by adjustment of surface charge associated with phase domain structures", Analytics Chimica Acta, (Abstract, pp. 1-2), (Year: 1992).*
Carbone, C., et al., "Preparation and optimization of PIT solid lipid nanoparticles via statistical factorial design", Eur. J,. Med. Chem., pp. 110-117 (Year: 2012).*
Tanmoy Saha et al., "Performance comparison of two cascade reaction models in fluorescence off-on detection of hydrogen sulfide", RSC Advances, 2015, pp. 1438-1446, vol. 5, The Royal Society of Chemistry.
Ajay Singh et al., "Bio-Lighted Nanotorch Capable of Systemic Self-Delivery and Diagnostic Imaging," ACS NANO, 2015, pp. 9906-9911, vol. 9.
Jeongyun Heo et al., "Fluorogenic Nanoreactor Assembly with Boosted Sensing Kinetics for Timely Imaging of Cellular Hydrogen Peroxide," ChemComm, 2015, pp. 1131-1134, vol. 52, DOI: 10.1039/C5CC06387F.
Myung Kim et al., "A fluorogenic molecular nanoprobe with an engineered internal environment for sensitive and selective detection of biological hydrogen sulfide," ChemComm, Jan. 26, 2017, pp. 2275-2278, vol. 53, The Royal Society of Chemistry.
Myung Kim et al., "A fluorogenic molecular nanoprobe with an engineered internal environment for sensitive and selective detection of biological hydrogen sulfide," Electronic Supplementary Information for ChemComm, 2017, 10 pages.

* cited by examiner

*Primary Examiner* — Michael G. Hartley
*Assistant Examiner* — Lance W Rider
(74) *Attorney, Agent, or Firm* — Cantor Colburn LLP

(57) ABSTRACT

The present invention relates to a nanocomposite for detecting hydrogen sulfide; a method for preparing the same; a novel reactive fluorogenic compound to be used in the method; a kit for detecting hydrogen sulfide comprising the nanocomposite; and a method for providing information for the diagnosis of a disease, which causes abnormal secretion of hydrogen sulfide, by using the nanocomposite.

12 Claims, 13 Drawing Sheets

(a)

(b)

(c)

REACTIVE FLUOROGENIC COMPOUND AND NANOCOMPOSITE FOR SENSING HYDROGEN SULFIDE COMPRISING THE SAME

TECHNICAL FIELD

The present invention relates to a nanocomposite for detecting hydrogen sulfide and a method for preparing the same; a novel reactive fluorogenic compound used therein and a method for preparing the same; a kit for detecting hydrogen sulfide comprising the nanocomposite; and a method for providing information for the diagnosis of a disease which causes abnormal secretion of hydrogen sulfide by using the nanocomposite.

BACKGROUND ART

Hydrogen sulfide ($H_2S$), a gasotransmitter produced endogenously from cysteine by enzymes such as cystathionine β-synthase (CBS), cystathionine γ-lyase (CSE), and 3-mercapto-pyruvate sulfurtransferase (3-MST), plays significant roles in the cardiovascular, immune, and nervous systems. While $H_2S$ is known to exert protective effects against oxidative stresses in many pathologies, abnormal levels thereof in cells, tissues, and plasma are implicated in various diseases including chronic kidney disease, liver cirrhosis, Down's syndrome, Alzheimer's disease, and diabetes. Although a number of reactions between highly reactive $H_2S$ and biological targets have been suggested, the detailed mechanisms are still unclear. Therefore, the sensitive detection of intracellular and in vivo $H_2S$ levels is essential for further understanding of its biological functions.

Among various chemosensing techniques, fluorescence detection has shown advantages for monitoring biological matters noninvasively in physiological environments with higher spatial-temporal resolution and lower background noise. In recent years, chemical reaction-based fluorogenic probes have been developed and applied to $H_2S$ detection in living cells and animal models. In the design of $H_2S$-responsive probes, various reaction strategies have been exploited, including nucleophilic addition, copper sulfide precipitation, azide reduction, etc. Although a number of small dye-based fluorogenic molecular probes have been reported as $H_2S$-responsive chemosensors, few multiple molecule-integrated nanoscale probes with fine-tuned sensitivity and selectivity have been developed so far.

Chinese Patent Application Publication No. CN 104403663 A discloses a fluorogenic probe for detecting endogenous $H_2S$, which is prepared by self-assembling BODInD and boron-dipyrromethene fluorophore from an amphiphilic surfactant. However, only a neutral surfactant was used, and thus the reaction between a hydrophobic fluorogenic probe and a hydrophilic sensor in an aqueous environment was not effectively improved.

Accordingly, the present inventors have made intensive efforts to devise a novel $H_2S$-responsive fluorogenic dye and to discover a nanocomposite structure capable of providing reaction conditions that can maximize sensitivity of the $H_2S$-responsive fluorogenic dye. As a result, they have invented a composite with a nanoprobe for $H_2S$ detection, which has a molecular composition precisely designed to create an internal environment optimized for the reaction detecting a hydrophilic sensor of a hydrophobic probe while using a hydrophobic molecular probe.

DISCLOSURE

Technical Problem

An objective of the present invention is to provide a nanocomposite for detecting hydrogen sulfide ($H_2S$).

Another objective of the present invention is to provide a method for preparing the nanocomposite.

Still another objective of the present invention is to provide a novel reactive fluorogenic compound or a pharmaceutically acceptable salt thereof.

Still another objective of the present invention is to provide a method for preparing the reactive fluorogenic compound.

Still another objective of the present invention is to provide a kit for detecting hydrogen sulfide comprising the nanocomposite.

Still another objective of the present invention is to provide a method for providing information for the diagnosis of a disease, which causes abnormal secretion of hydrogen sulfide, by using the nanocomposite.

Technical Solution

A first aspect of the present invention provides a nanocomposite for detecting hydrogen sulfide ($H_2S$) comprising a $C_{10-25}$ alkane or haloalkane, a neutral first surfactant, a cationic second surfactant, and a reactive fluorophore, wherein: the nanocomposite is self-assembled by co-assembly of the first surfactant and the second surfactant, in which the self-assembly comprises a hydrophobic core containing a $C_{10-25}$ alkane or haloalkane and the hydrophobic core comprises a reactive fluorophore, wherein the reactive fluorophore itself is non-fluorescent but exhibits fluorescence by a reaction with hydrogen sulfide.

A second aspect of the present invention provides a method for preparing the nanocomposite of any one of claims 1 to 9, comprising a first step of mixing a mixture of $C_{10-25}$ alkane or haloalkane and a reactive fluorophore dissolved in an organic solvent with a mixed aqueous solution comprising a neutral first surfactant and a cationic second surfactant.

A third aspect of the present invention provides a compound represented by the Formula 1 or a pharmaceutically acceptable salt thereof:

[Formula 1]

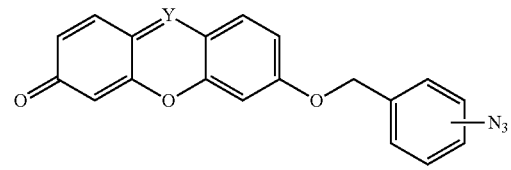

wherein, in the above formula,
Y is N or CR; and
R is carboxyphenyl.

A fourth aspect of the present invention provides a method for preparing the compound of Formula 1, comprising mixing and reacting a first solution, in which a compound represented by Formula 2 below, which comprises a hydroxyl group at $C_7$, is dissolved in an organic solvent, with a second solution in which azido(halomethyl)benzene is dissolved in an organic solvent:

[Formula 2]

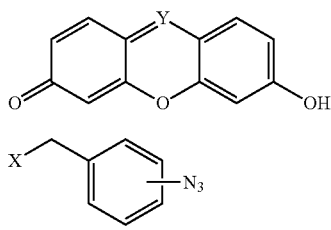

[Formula 3]

wherein, in the above formulas,
Y is N or CR;
R is carboxyphenyl; and
X is halogen.

A fifth aspect of the present invention provides a kit for detecting hydrogen sulfide comprising the nanocomposite.

A sixth aspect of the present invention provides a method for providing information for the diagnosis of a disease causing abnormal secretion of hydrogen sulfide, comprising: a first step of contacting the nanocomposite with a specimen isolated from a subject suspected of having a disease; a second step of measuring a fluorescence spectrum of a sample obtained from the first step; and a third step of deriving the concentration of hydrogen sulfide in the specimen from the fluorescence spectrum obtained from the second step.

Hereinbelow, the present invention will be described in detail.

The present invention is based on devising a novel compound for the selective detection of hydrogen sulfide, which is a gasotransmitter playing a significant role in the cardiovascular, immune, and nervous systems and which can be an index for diagnosing diseases such as chronic kidney disease, liver cirrhosis, Down's syndrome, Alzheimer's disease, and diabetes; and on discovering a nanocomposite capable of providing an environment for more sensitive detection of the compound.

Specifically, the present invention is characterized in that in the compound, resorufin, which becomes a non-fluorescent molecule by losing its native fluorescence when a substituent is bound to a specific position and which recovers its fluorescence by chemoselective nucleophilic reduction of active $HS^-$ ions provided from hydrogen sulfide, is selected as a precursor, thereby devising a novel reactive fluorophore in which an azidoaryl linker is bound to the 7-hydroxy position of the resorufin.

Additionally, the present invention is characterized in that in order to improve the reactivity of the reactive fluorophore, a form of a micelle-supported nanocomposite is provided, but the nanocomposite is co-assembled using a neutral surfactant together with a cationic surfactant to regulate the degree of charging of the nanocomposite surface, and thus the accessibility of the analyte is improved and the core further includes a hydrophobic medium; therefore, inside the core, the hydrophobic portion of the cationic surfactant used as the co-surfactant, as well as the reactive fluorophore molecule, are stably maintained.

In the nanocomposite of the present invention, the $C_{10-25}$ alkane or haloalkane may be 1-iodooctadecane, but is not limited thereto. As described above, the $C_{10-25}$ alkane or haloalkane may be added to stably contain hydrophobic portions of the reactive fluorophore and cationic surfactant inside the nanocomposite, but is not limited to the chemical species above as long as this objective can be achieved.

For example, in the nanocomposite of the present invention, the first surfactant may be 1,2-distearoyl-sn-glycero-3-phosphoethanolamine)-N-methoxy(polyethylene glycol) (DSPE-PEG), and the second surfactant may be stearalkonium chloride (SKC), but these are not limited thereto.

In the nanocomposite of the present invention, the reactive fluorophore may be a molecule that is cleaved by a reduction reaction with $HS^-$ ions and decomposed into a fluorescent molecule and an aryl azide linker. Specifically, the reactive fluorophore may be azidobenzylresorufin (ABR) in which a hydroxy (—OH) position, the $7^{th}$ position of resorufin, is substituted with azidobenzyl; or azidobenzylfluorescein in which a hydroxy (—OH) position, the $7^{th}$ position of fluorescein, is substituted with azidobenzyl. The resorufin or fluorescein comprised in the reactive fluorophore contained in the nanocomposite of the present invention may lose or acquire fluorescence depending on the presence of a substituent at position 7. For example, resorufin or fluorescein itself has fluorescence, but in a molecule in which a substituent is introduced at the 7-hydroxy position, fluorescence is absent. However, when the substituent is removed, the original fluorescence can be recovered.

The nanocomposite of the present invention may comprise the first surfactant and the second surfactant in a weight ratio of 10:90 to 50:50, but is not limited thereto. For example, if the weight ratio of the second surfactant to the first surfactant is less than the range above, the reactivity may be low, and thus the formation of a desired composite may be difficult. In addition, if the weight ratio exceeds the range above, the toxicity may be increased, and thus the possibility of use for biomedical purposes may be reduced.

The nanocomposite of the present invention may comprise the reactive fluorophore in an amount of 1 to 30 parts by weight based on 100 parts by weight of the first surfactant, but is not limited thereto. For example, if the amount of the reactive fluorophore used is higher or lower than the range above, the stability of particles to be formed may actually be reduced.

The nanocomposite of the present invention may comprise the $C_{10-25}$ alkane or haloalkane in an amount of 20 wt % to 50 wt % (or mol %, etc.) based on the weight of the reactive fluorophore, but is not limited thereto. For example, if the amount of the $C_{10-25}$ alkane or haloalkane is higher or lower than the range above, the stability of particles to be formed may actually be reduced.

Meanwhile, the nanocomposite of the present invention may be prepared by a method comprising a first step of mixing a mixture of a $C_{10-25}$ alkane or haloalkane and a reactive fluorophore dissolved in an organic solvent with a mixed aqueous solution comprising a neutral first surfactant and a cationic second surfactant.

Herein, the organic solvent may be used in an amount of 0.2 vol % (v/v) to 5 vol % (v/v) relative to the aqueous solution, but is not limited thereto. For example, if the amount of the organic solvent used is higher or lower than the range above, the stability of particles as well as the reactivity may be lowered, and thus it may be disadvantageous to sensitive detection.

The preparation method of the present invention may provide an aqueous dispersion solution in which the nanocomposite is evenly dispersed in an aqueous solution.

Further, the present invention provides a compound of Formula 1 or a pharmaceutically acceptable salt thereof:

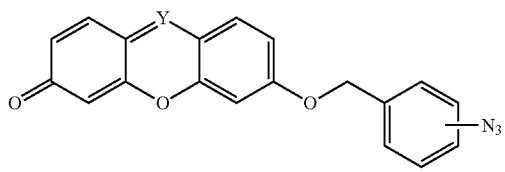

[Formula 1]

wherein, in the above formula,
Y is N or CR; and
R is carboxyphenyl.

For example, the compound may be 1) 7-(4-azidobenzyloxy)-3H-phenoxazin-3-one; or 2) 2-(6-(4-azidobenzyloxy)-3-oxo-3H-xanthen-9-yl)benzoic acid.

The compound may be cleaved by a reduction reaction with HS⁻ ions provided from hydrogen sulfide and decomposed into an aryl azide linker and resorufin, which is a fluorescent molecule, and as a result, may generate fluorescence of resorufin selectively with respect to hydrogen sulfide, e.g., HS⁻ ions.

The compound of the present invention may exist in the form of a salt, especially a pharmaceutically acceptable salt. Salts that are conventionally used in the art, such as acid addition salts produced from pharmaceutically acceptable free acids, can be used without limitation. As used herein, the term "pharmaceutically acceptable salt" refers to any organic or inorganic compound addition salt whose concentration has effective action because it is relatively non-toxic and harmless to the patients and whose side effects do not degrade the beneficial efficacy of the compound which is represented by Formula 1.

Acid addition salts are prepared in the conventional way, for example, by dissolving the compound in an excessive quantity of an aqueous solution of the acid followed by the precipitation of the resultant salt using a water-miscible organic solvent such as methanol, ethanol, acetone, or acetonitrile. The compound of the same molar amount and acid or alcohol in water (e.g., glycol monomethyl ether) can be heated and subsequently, the resultant mixture can be dried by evaporating, or precipitated salts can be filtered by suction.

Herein, organic acids and inorganic acids can be used as the free acid. Available inorganic acids may be, but are not limited to, hydrochloric acid, phosphoric acid, sulfuric acid, nitric acid, and tartaric acid; and available organic acids may be, but are not limited to, methanesulfonic acid, p-toluene sulfonic acid, acetic acid, tri-fluoro acetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, pharmaceutically acceptable metal salts can be prepared using a base. For example, alkali metal salts or alkali earth metal salts are obtained by dissolving the compound in an excess of an alkali metal hydroxide or alkali earth metal hydroxide solution, filtering the undissolved compound salt, and drying the filtrate by evaporation. Herein, sodium, potassium, or calcium salts are pharmaceutically suitable for preparation as a metal salt, but are not particularly limited thereto. In addition, the corresponding silver salt can be obtained by reacting an alkali metal or alkali earth metal salt with a suitable silver salt (for example, silver nitrate).

Pharmaceutically acceptable salts of the compound in Formula 1 include, unless otherwise indicated, salts of an acid or alkali group that may be present in the compound in Formula 1. For example, pharmaceutically acceptable salts may include sodium, calcium, and potassium salts of a hydroxy group and other pharmaceutically acceptable salts of an amino group may include hydrobromide, sulfate, hydrogen sulfate, phosphate, hydrogen phosphate, dihydrogen phosphate, acetate, succinate, citrate, tartrate, lactate, mandelate, methane sulfonate (mesylate), and p-toluene sulfonate (tosylate) salts and can be prepared by the preparation method for salts known in the art.

As the pharmaceutically acceptable salts of the compound of the present invention, which is represented by Formula 1, any salts of a compound which exhibits fluorescence through a H₂S-selective reduction reaction equivalent to that of the compound of Formula 1 may be used without limitation.

Additionally, the present invention provides a method for preparing the compound of Formula 1, comprising mixing and reacting a first solution, in which a compound represented by Formula 2 below, which comprises a hydroxyl group at C₇, is dissolved in an organic solvent, with a second solution in which azido(halomethyl)benzene is dissolved in an organic solvent:

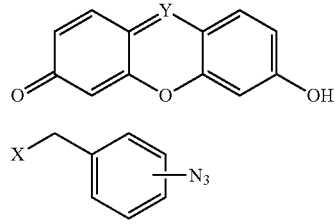

[Formula 2]

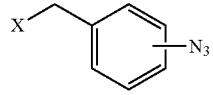

[Formula 3]

wherein, in the above formulas,
Y is N or CR; R is carboxyphenyl; and X is halogen.

Specifically, the first solution may further comprise a basic additive. For example, the basic additive may be K₂CO₃, Cs₂CO₃, Na₂CO₃, triethylamine (TEA), trimethylamine (TMA), pyridine, or a combination thereof, but is not limited thereto.

Specifically, the organic solvent may be a polar aprotic solvent. For example, the organic solvent may be dimethylfuran (DMF), tetrahydrofuran (THF), acetonitrile (MeCN), acetone, dimethyl sulfoxide (DMSO), N-methyl-2-pyrrolidone (NMP), or a mixture thereof, but is not limited thereto.

For example, the reaction may be carried out by stirring at 35° C. to 70° C. for 2 hours to 5 hours, but is not limited thereto.

After completion of the reaction, steps of washing and drying may be further included, but the steps are not limited thereto. The step of washing and/or drying may be carried out by any method known in the art without limitation.

Additionally, the present invention provides a kit for detecting hydrogen sulfide comprising the nanocomposite and a method for diagnosing a disease, which is accompanied by abnormal secretion of hydrogen sulfide, by using the kit.

As described above, since the nanocomposite according to the present invention or the kit comprising the same can selectively or sensitively detect hydrogen sulfide, it can be effectively used for diagnosing a disease accompanied by abnormal secretion of hydrogen sulfide, such as chronic kidney disease, cirrhosis, Down's syndrome, Alzheimer's disease, or diabetes.

Specifically, the diagnostic method using the nanocomposite of the present invention may be a method for providing information for the diagnosis of a disease causing abnormal secretion of hydrogen sulfide, comprising: a first step of contacting the nanocomposite with a specimen isolated from a subject suspected of having a disease; a second step of measuring a fluorescence spectrum of the sample obtained from the first step; and a third step of deriving the concentration of hydrogen sulfide in the specimen from the fluorescence spectrum obtained from the second step.

For example, the disease causing abnormal secretion of hydrogen sulfide, which can be diagnosed by using the method of using the nanocomposite according to the present invention, may be chronic kidney disease, cirrhosis, Down's syndrome, Alzheimer's disease, or diabetes, but the disease is not limited thereto. In addition, it can be applied without limitation to the diagnosis of a disease accompanied by a decrease or increase in a hydrogen sulfide level in the sample isolated from the subject compared to that of a normal subject.

As used herein, the "subject" refers to all kinds of animals including humans, monkeys, cattle, horses, sheep, pigs, chickens, turkeys, quails, cats, dogs, mice, rabbits, and guinea pigs which have already developed or are at risk of developing the disease causing abnormal secretion of hydrogen sulfide.

In the method of the present invention for providing information for the diagnosis, the second step of measuring a fluorescence spectrum can be carried out by using a conventional spectrophotometer or by using a home-built device. For example, it can be carried out by irradiating with light of a wavelength selected from the range of 500 nm to 600 nm in which the absorption spectrum of resorufin exists, and specifically selected from the range of 530 nm to 585 nm including the maximum absorption wavelength (572 nm); alternately, it can be carried out by scanning in the range of 550 nm to 650 nm exhibiting the fluorescence spectrum, or by detecting the fluorescence intensity at a wavelength selected from 586 nm, which is the maximum fluorescence wavelength, or the range of 570 nm to 600 nm including the maximum fluorescence wavelength, but is not limited thereto.

Further, the third step of deriving the concentration of hydrogen sulfide from the fluorescence spectrum obtained can be carried out using the following equation through linear regression analysis:

$$Y=a+bx \quad \text{[Equation 1]}$$

In the Equation above, Y represents fluorescence intensity after the reaction, a represents a constant, b represents slope, and x represents concentration of hydrogen sulfide. That is, since the concentration of hydrogen sulfide exhibits a direct relationship with the fluorescence intensity after the reaction, the concentration of hydrogen sulfide can be derived by deriving a calibration curve of the fluorescence intensity according to the concentration by using a standard sample having two or more different concentrations, followed by substituting the fluorescence values measured from an unknown sample, e.g., a biological sample.

Herein, data analyzed by the same method using a sample isolated from a normal subject can be used as a control group.

For example, it is reported in the art that the plasma hydrogen sulfide level in diabetic patients is lower than that in normal individuals, indicating that the plasma hydrogen sulfide level can be a criterion for diabetes diagnosis. S. K. Jain et al. reported that the average plasma hydrogen sulfide concentration in normal individuals is 130 μM, whereas that in diabetic patients is 110 μM (Antioxid. Redox Signal., 2010, 12(11): 1333-1337). Accordingly, when the plasma hydrogen sulfide concentration derived by applying the diagnostic method using a blood sample as a specimen is 120 μM or below, or specifically 115 μM or below, the subject can be judged to be a patient having diabetes.

Advantageous Effects

The novel self-sacrificing fluorophore of the present invention includes a resorufin moiety and an aryl azide linker which acquire or lose fluorescence depending on the presence of a substituent at a specific position, and thus it is useful for the detection of a change in the hydrogen sulfide level because the fluorophore which has non-fluorescence exhibits fluorescence when separated into resorufin and an aryl azide linker by a selective reduction reaction with hydrogen sulfide. In particular, when the nanocomposite formed by further including the cationic surfactant according to the present invention comprises the self-sacrificing fluorophore together with a hydrophobic solvent, the reduction reaction is regulated, and thus more sensitive detection is possible. Accordingly, the nanocomposite may be effectively used for the diagnosis of a disease accompanied by abnormal secretion of hydrogen sulfide.

BRIEF DESCRIPTION OF DRAWINGS

FIG. 12a is bright field/fluorescence images of HeLa cells treated with nanoABR (4×10$^{-5}$ M) for 1 hour: (i) probe alone, (ii) probe+inhibitor (PAG), and (iii) probe+inducer (SNP).

FIG. 12b is a graph showing the spectral profiles (left) and the relative intensities (right) of cytosolic fluorescence in FIG. 12a.

FIG. 14a is a diagram showing the fluorescence from nanoABR taken 30 minutes after mixing with sera from diabetes or normal mice (Ex 535 nm/Em 600 nm). Sera without mixing with nanoABR were only used as a control group.

FIG. 14b is a graph showing the absolute values of the fluorescence intensities observed in FIG. 14a.

FIG. 14c is a graph showing the control-normalized relative values for the fluorescence intensities observed in FIG. 14a.

DETAILED DESCRIPTION OF THE INVENTION

Hereinbelow, the present invention will be described in detail with accompanying exemplary embodiments. However, the exemplary embodiments disclosed herein are only for illustrative purposes and should not be construed as limiting the scope of the present invention.

<Materials and Instrumentation>

All chemical reagents were purchased from Aldrich and TCI and used without purification. DSPE-PEG-2000 (1,2-distearoyl-sn-glycero-3-phosphoethanolamine-N-[methoxy(polyethylenegly-col)]) was purchased from Avanti Polar Lipids, Inc. 4-Azidobenzyl bromide was synthesized by a method known in the art (H. Zhang et al., Talanta, 2015, 135: 149-154). $^1$H NMR and $^{13}$C NMR spectra of the synthesized compounds were recorded on a Bruker AVANCE 400 spectrometer. Elemental analysis was carried out using a FLASH 2000 (Thermo SCIENTIFIC, England) CHNS analyzer. Absorption and photoluminescence spectra were recorded on a UV-visible spectrometer (Agilent 8453) and the F-7000 fluorescence spectrophotometer (Hitachi, wavelength calibrated for excitation and emission), respectively. The nanoparticle size distribution was determined by a dynamic light scattering (DLS) method using a particle sizer (90Plus, Brookhaven Instruments Corporation)) at 25° C.

Example 1: Synthesis of ABR

Resorufin (50 mg, 0.145 mmol) and K$_2$CO$_3$ (40 mg, 0.29 mmol) were dissolved in DMF (4 mL) and stirred at room temperature under an argon atmosphere. After the solution color changed to dark purple, 4-azidobenzyl bromide (61.5 mg, 0.29 mmol) dissolved in DMF (1 mL) was added dropwise to the stirred solution. The reaction mixture was stirred at 50° C. for 3 hours. After cooling to room temperature, the reaction mixture was poured into brine and extracted with ethyl acetate two times. The organic layer was separated and dried over anhydrous MgSO$_4$. The solvent was evaporated at reduced pressure, and the residue was purified by column chromatography on silica gel with ethyl acetate/n-hexane 1:1 (v/v). ABR (35 mg) was obtained as an orange solid in 70.3% yield.

$^1$H NMR (400 MHz, CDCl$_3$, δ): 7.72-7.70 (d, J=8.8 Hz, 1H), 7.42-7.39 (m, J=8.4 Hz and 10.0 Hz, 3H), 7.07-7.05 (d, J=8.4 Hz, 2H), 6.99-6.97 (dd, J=8.8 Hz and 2.8 Hz, 1H), 6.86-6.85 (d, J=2.4 Hz, 1H), 6.84-6.81 (dd, J=10.0 Hz and 2.0 Hz, 1H), 6.30 (d, J=2.0 Hz, 1H), 5.12 (s, 2H);

$^{13}$C NMR (150 MHz, CDCl$_3$, δ): 186.34, 162.47, 149.82, 145.76, 145.64, 140.47, 134.74, 134.34, 132.03, 131.70, 129.19, 128.59, 119.44, 114.24, 106.80, 101.07, 70.32;

Anal. calcd for C$_{19}$H$_{12}$N$_4$O$_3$: C 66.28, H 3.51, N 16.27; found: C 66.10, H 4.13, N 15.47.

Figure 1:
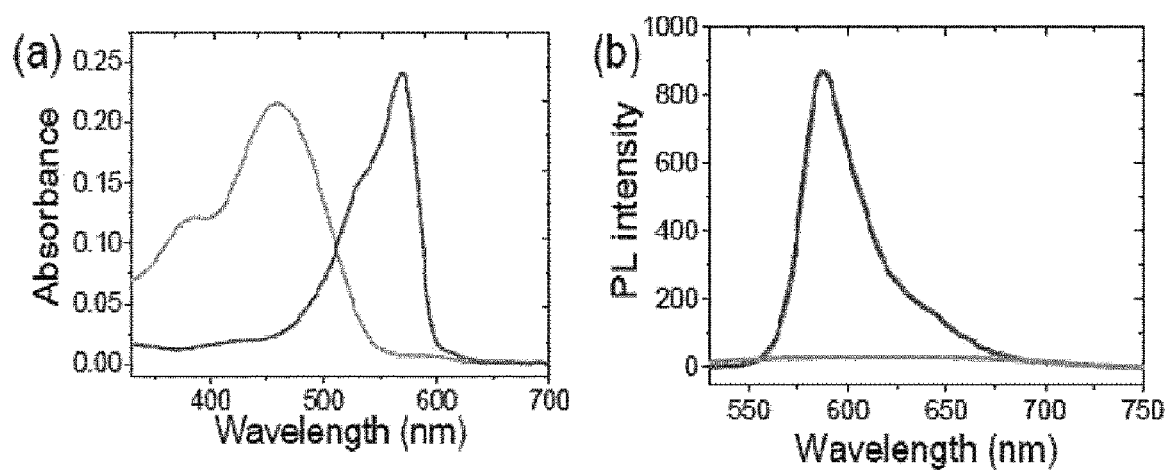
FIGS. 1a and 1b are graphs showing the absorption of resorufin (red curve) and ABR (orange curve) dissolved in DMSO and the fluorescence spectra at an excitation wavelength of 480 nm, respectively.
Figure 2:
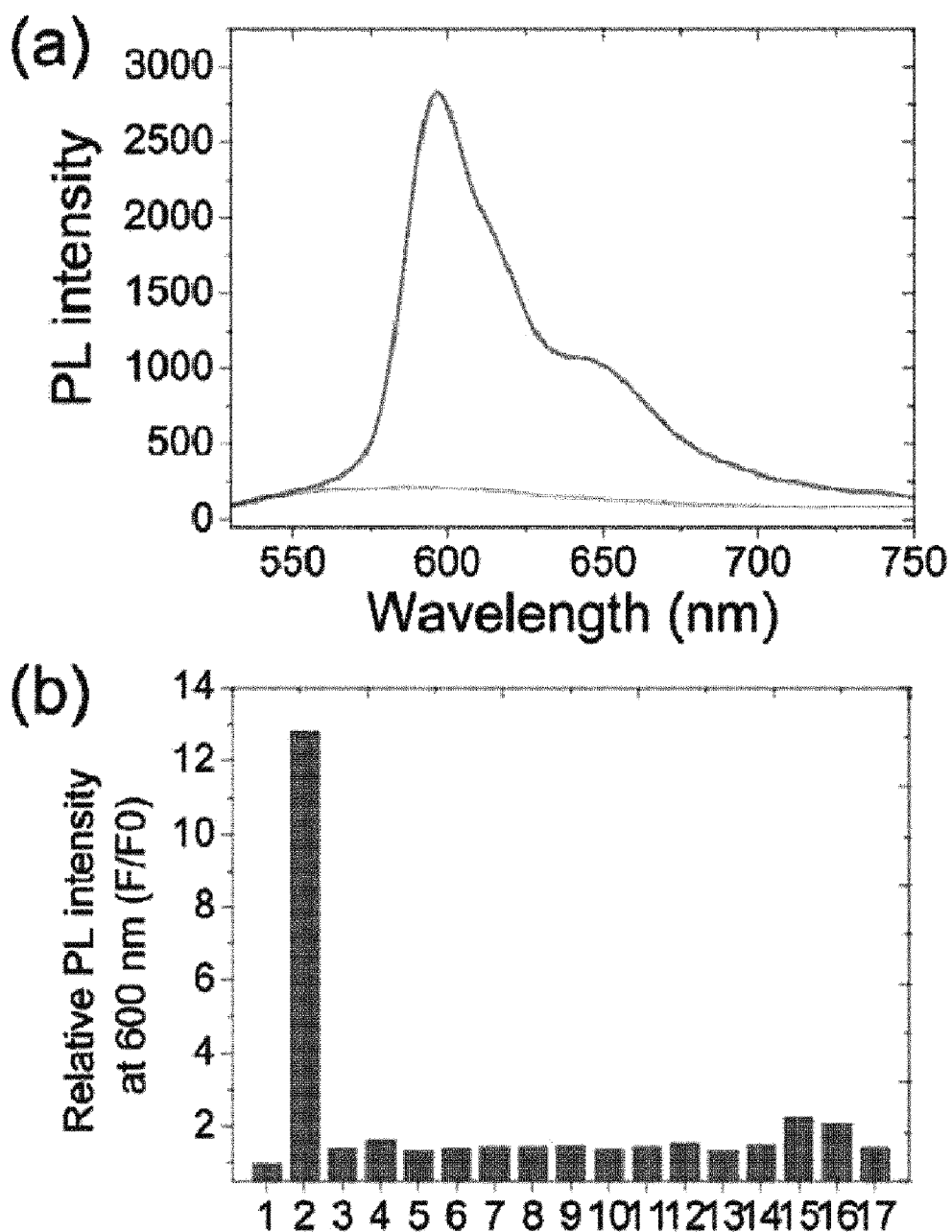
FIG. 2a is a graph showing fluorescence spectral changes of ABR in an environment where NaHS is absent (orange curve) or present (red curve).
FIG. 2b is a graph showing the fluorescence intensity of ABR in the presence of various reactive species (100 μM unless specified otherwise): (1) ABR only; (2) NaHS; (3) SCN$^-$; (4) GSNO; (5) GSH (1 mM); (6) SO$_3^{2-}$; (7) S$_2$O$_3^{2-}$; (8) L-cysteine; (9) homo-cysteine; (10) H$_2$O$_2$; (11) TBHP; (12) O$_2^-$; (13) OCl$^-$; (14) NO.; (15) ClO$_4^-$; (16) OH.; and (17) t-BuO.
Figure 3:
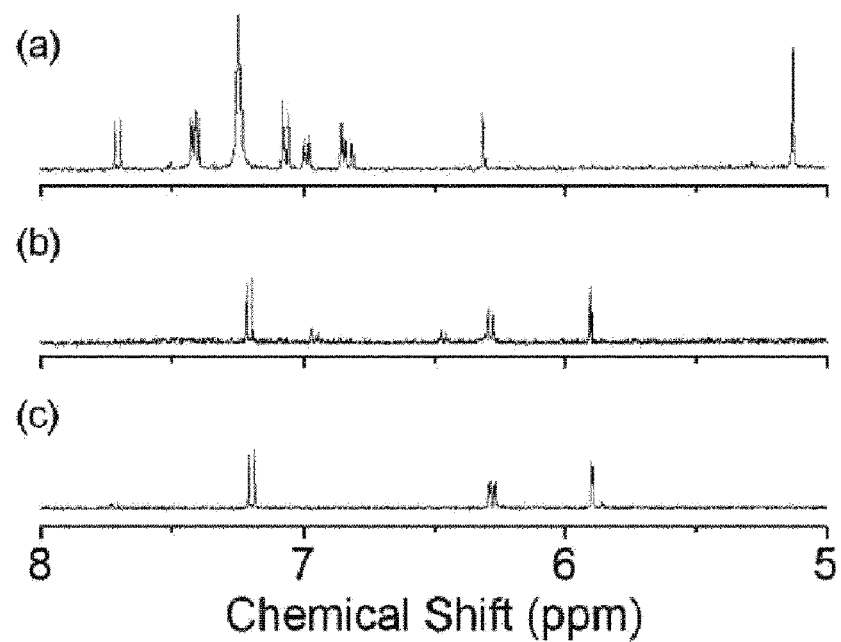
FIG. 3a is a graph showing $^1$H-NMR spectra of ABR in CDCl$_3$.
FIG. 3b is a graph showing $^1$H-NMR spectra of ABR after reaction with H$_2$S in DMSO-d$_6$.
FIG. 3c is a graph showing $^1$H-NMR spectra of resorufin sodium salt in DMSO-d$_6$.

Specifically, in order to devise a H$_2$S-responsive fluorogenic molecular probe, the present inventors have adopted a reaction strategy based on the chemoselective reduction of aryl azides to amines, which is triggered through nucleophilic attack by a hydrosulfide anion (HS$^-$), which is the main active form of H$_2$S under physiological conditions. In the probe design, the 4-azidobenzyl group was selected as a self-immolative aryl azide linker, and it was linked to a fluorescent emitter, resorufin, at its 7-hydroxy position. Since the 7-hydroxy substituent is known to efficiently quench the fluorescence of resorufin, the designed molecular probe, azidobenzylresorufin (ABR), is anticipated to be nonfluorescent and able to undergo self-immolative cleavage upon reaction with HS$^-$, to release a 1,6-elimination product (azaquinone methide) and resorufin with fluorescence recovery. Indeed, the obtained ABR probe that is water-soluble was shown to be virtually nonfluorescent with a hypsochromic absorption shift compared to resorufin in organic media (FIG. 1). As expected from the design, it presented a fluorescence turn-on response toward H$_2$S (FIG. 2a). Along the resulting fluorescence spectrum, the $^1$H-NMR analysis confirmed that the fluorescent product is resorufin recovered through the self-immolative release from ABR after reduction by H$_2$S (FIG. 3). ABR exhibited high chemoselectivity in spectroscopic response; when treated with various biologically relevant reaction sulfur, oxygen, and nitrogen species in acetonitrile, ABR responded only to H$_2$S with substantial recovery of the resorufin fluorescence (FIG. 2b; not even responsive to excess GSH at a physiologically relevant concentration of 1 mM).

Example 2: Preparation of nanoABR for $H_2S$ Detection Using ABR as Fluorescent Molecule Nanoprobe ABR (0.014 mg) was homogeneously mixed with 1-iodooctadecane (0.005 mg) in a THF (0.2 mL) solvent. After the solvent was evaporated by air flow, the dried mixture was homogeneously dissolved in DMSO (10 μL) and mixed with Milli-Q water (990 μL) containing DSPE-PEG (0.1 mg) with or without stearalkonium chloride (SKC, 0.4 mg) with vigorous shaking to obtain an aqueous dispersion solution of self-assembled nanoABR. The other nanoABR probes co-assembled with differently charged co-surfactant molecules were prepared by following the same procedure with F127 (5 mg) or sodium dodecyl sulfate (0.5 mg) instead of SKC.

Comparative Example 1: Preparation of nanoABR Including Neutral Pluronic as Co-Surfactant NanoABR was prepared in the same manner as in Example 2 except that neutral Pluronic (F127) was used instead of SKC as the co-surfactant.

Comparative Example 2: Preparation of nanoABR Including Anionic SDS as Co-Surfactant NanoABR was prepared in the same manner as in Example 2 except that anionic sodium dodecyl sulfate (SDS) was used instead of SKC as the co-surfactant.

Example 3: Effect of Co-Surfactant on Polarity of Composite

Figure 4:
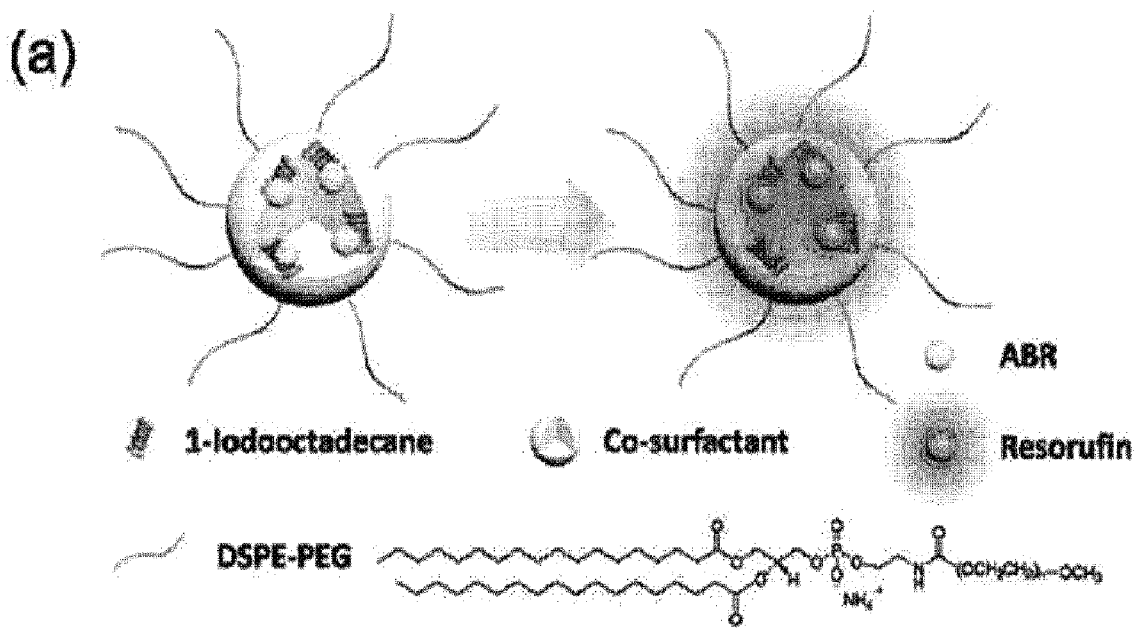
FIG. 4a is a diagram schematically showing the shape and operation principle of nanoABR.
FIG. 4b is a graph showing the change in fluorescence intensity of nanoABR depending on the co-assembled surfactants before (black) and after (red) the addition of NaHS in a PBS buffer.
FIGS. 4c and 4d are graphs showing the fluorescence intensity of nanoABR over time in the presence of NaHS (100 μM).
FIG. 4e is a graph showing the intensity of recovered nanoABR fluorescence depending on the concentration of NaHS.
Figure 4:
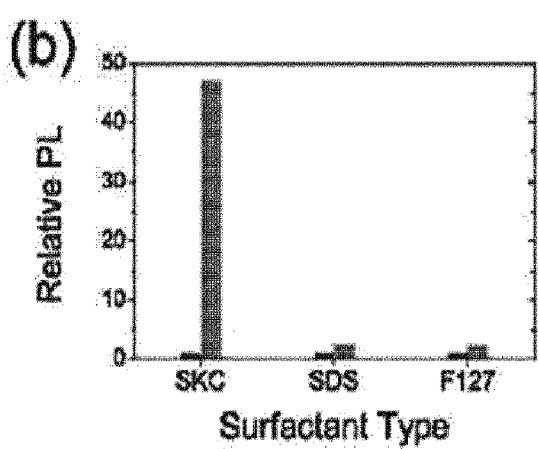
Figure 4:
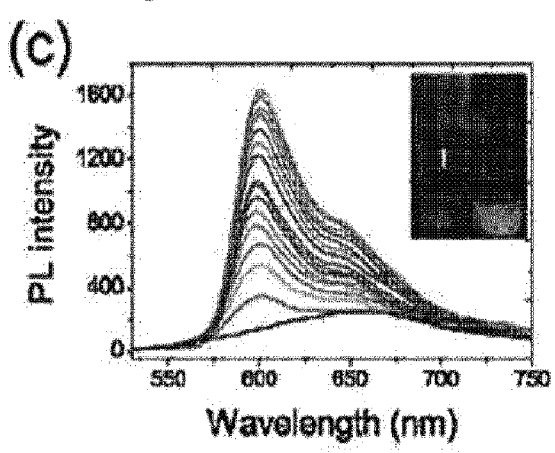
Figure 4:
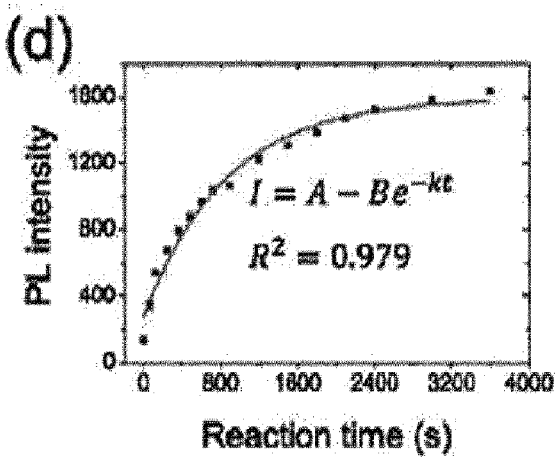
Figure 4:
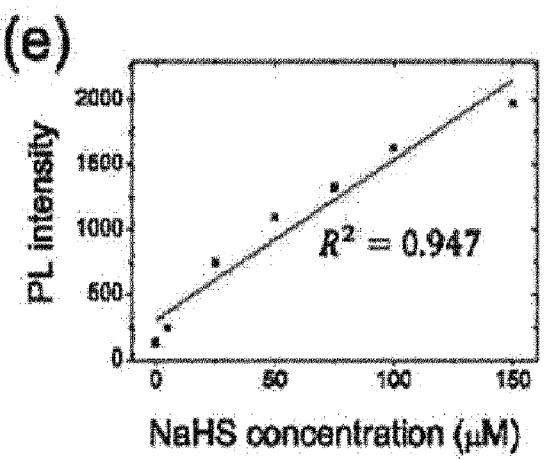
Figure 5:
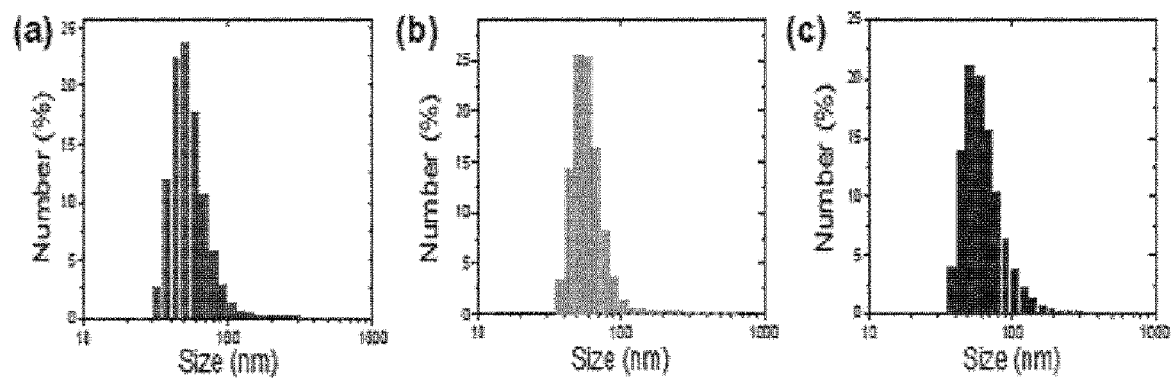
FIGS. 5a, 5b, and 5c are graphs showing number-averaged hydrodynamic size distributions of nanoABR co-assembled with each of (a) SKC, (b) SDS, and (c) F127.

In order to apply the water-insoluble ABR to aqueous physiological media, it was formulated into a water-dispersed nanoreactor probe (nanoABR), as depicted in Example 1 and Comparative Example 1 or 2. As shown in FIG. 4a, nanoABR is a nano-scale molecular composite that is composed of DSPE-PEG and 1-iodooctadecane with or without a co-surfactant, and loaded inside with ABR. Prior to optimization of the nanoreactor probe, the nanoscopic polarity effect on the sensing reactivity of the embedded ABR was evaluated. Specifically, as in Example 2, and Comparative Examples 1 and 2, surfactants for co-assembly were selected among differently charged materials, such as cationic SKC (Example 2), neutral F127, and anionic SDS. Through such additional surfactants, i.e., co-assembly including co-surfactants, the interface between the hydrophobic core surface of nanoABR and the surrounding medium was allowed to be differently charged to impose different polarity influences on the nearby core area where ABR is embedded. Nanoassembly with each co-surfactant yielded a stable aqueous dispersion solution of nanoABR probes, all with similar colloidal sizes (50 nm to 60 nm in hydrodynamic diameter, FIG. 5).

FIG. 4b shows the surfactant-dependent fluorescence reactivity of nanoABR to $H_2S$ in a PBS buffer. The parent nanoABR probe without additional co-surfactant assembly showed a very poor response, as opposed to the evident sensing behavior shown by ABR itself in organic media. Similarly, co-assembly with F127 that is electrically as neutral as DSPE-PEG in the parent nanoprobe only showed about 2.3-fold improvement in the fluorescence reactivity to $H_2S$. Considering the fact that the medium effects induced within micelles retard the nucleophilic reaction therein, the poor reactivity of ABR in the nanoABR probe is attributable to the low polarity originating from 1-iodooctadecane in the inner hydrophobic core that may be lower than those of the polar organic media used in FIG. 2. Additionally, it can be considered that the resulting less polar medium within the nanoreactor may prevent the access of a polar sensing analyte from the surrounding aqueous medium to the ABR molecules entrapped inside. When anionic SDS was co-assembled, no notable alteration in the reactivity was observed, with negligibly increased fluorescence intensity (2.6-fold). Form these results, it can be speculated that the interfacial negative charges given by the anionic head group of SDS would favorably increase the internal medium polarity of nanoABR near the surface, but at the same time, they could electrostatically repel an anionic active form of $H_2S$ ($HS^-$), and thus apparently result in no net influence on the reactivity due to these opposite effects. In contrast, it was shown that the co-assembly with cationic SKC greatly enhances the $H_2S$-responsive fluorescence recovery from nanoABR (47-fold). Such greatly enhanced reactivity may contribute to the following two favorable effects from SKC: (1) the electrostatic attraction by which the positively charged surface can actively recruit the oppositely charged monoanionic $HS^-$ into the nanoreactor to increase the analyte concentration inside, and (2) the cationic charge-induced polarity in the near-surface nanoreactor medium that can stabilize the anionic polar transition state $[ABR-SH]^-$ by the favorable electrostatic interaction.

Example 4: $H_2S$ Selectivity Evaluation of nanoABR

For selectivity studies, nanoABR was prepared for the titration of biological reactive species in a PBS buffer at pH 7.4. The stock solution (100 μM) of reactive sulfur species (RSS) was also prepared using a PBS buffer. The stock solutions (100 μM) of reactive oxygen species (ROS) such as $H_2O_2$, tert-butyl hydroperoxide (TBHP), and $OCl^-$ were provided as 30 wt %, 70 wt %, and 5 wt % aqueous solutions, respectively. NO. was produced by adding stock solution of 3-(aminopropyl)-1-hydroxy-3-isopropyl-2-oxo-1-triazene (NOC-5) dissolved in DMSO. $O_2^{-\cdot}$ was obtained from $KO_2$ in DMSO containing 0.2 M 18-crown-6 ether for increasing solubility of $KO_2$. OH. and t-BuO. were produced by Fenton reaction of $Fe^{2+}$ (1 mM) with $H_2O_2$ (100 μM) and TBHP (100 μM), respectively.

Figure 6:
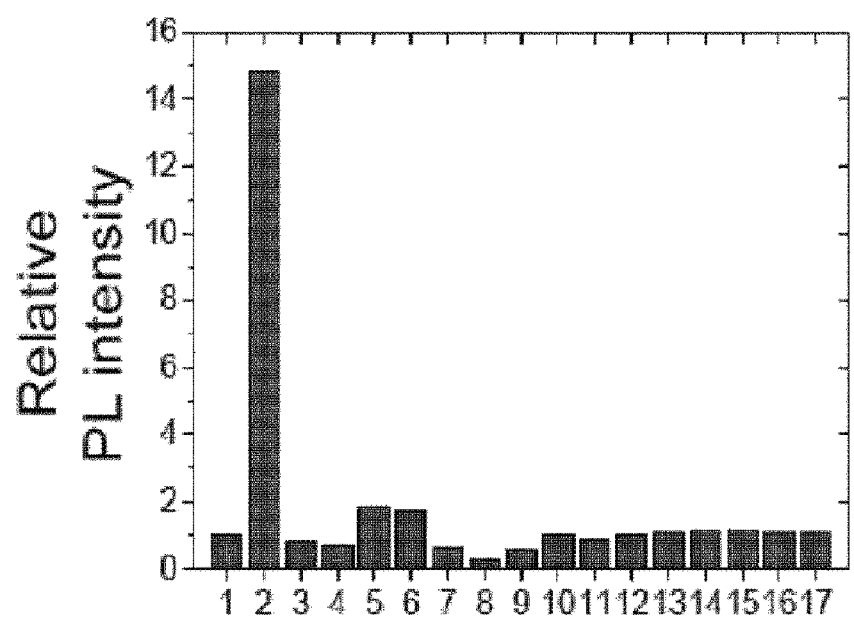
FIG. 6 is a graph showing the fluorescence intensity of nanoABR in a PBS buffer in the presence of various reactive species (100 μM unless specified otherwise): (1) ABR only; (2) NaHS; (3) SCN$^-$; (4) GSNO; (5) GSH (1 mM); (6) SO$_3^{2-}$; (7) S$_2$O$_3^{2-}$; (8) L-cysteine; (9) homo-cysteine; (10) H$_2$O$_2$; (11) TBHP; (12) O$_2^-$; (13) OCl$^-$; (14) NO.; (15) ClO$_4^-$; (16) OH.; and (17) t-BuO.
Figure 7:
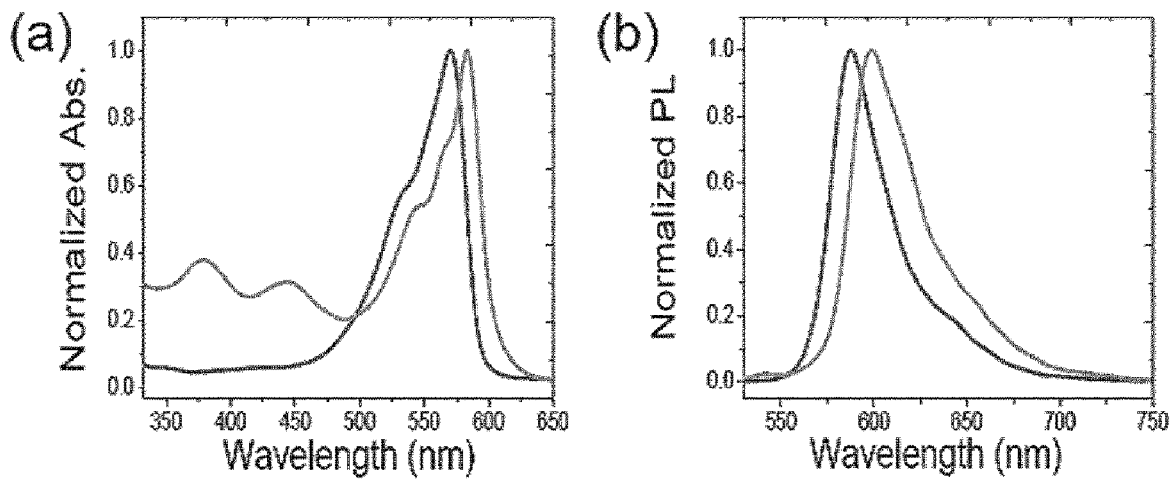
FIG. 7 is graphs showing the absorption (a) and fluorescence (b, excited at 480 nm) spectra of resorufin. The red curves indicate the spectra of resorufin in water and the orange curves indicate the spectra of nanoABR after reaction with H$_2$S in a PBS buffer.
Figure 8:
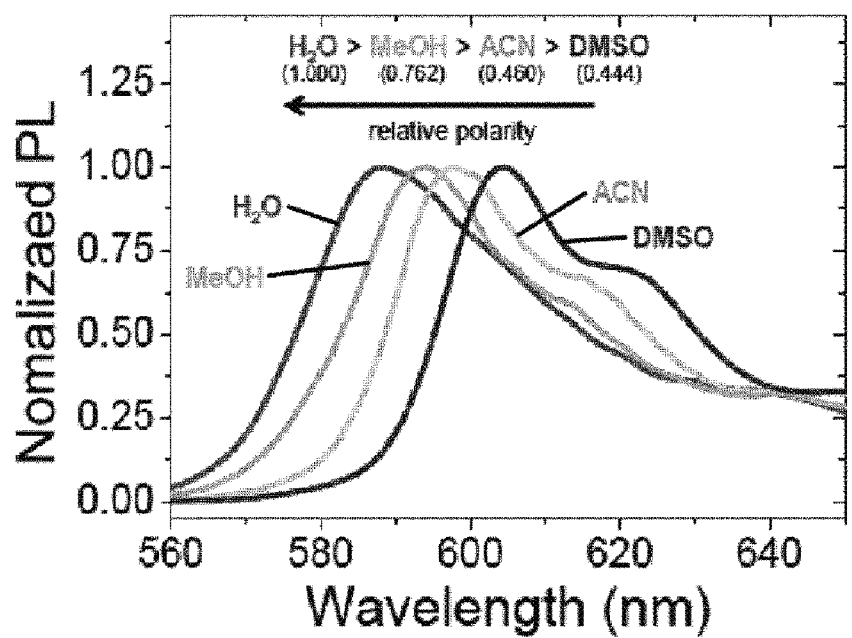
FIG. 8 is a graph showing the normalized florescence spectra of resorufin in various solvents, (red) H$_2$O; (green) methanol; (sky blue) acetonitrile; (blue) dimethylsulfoxide. The observed polarity-dependent peak shift indicates that resorufin has negative solvatochromism.
Figure 9:
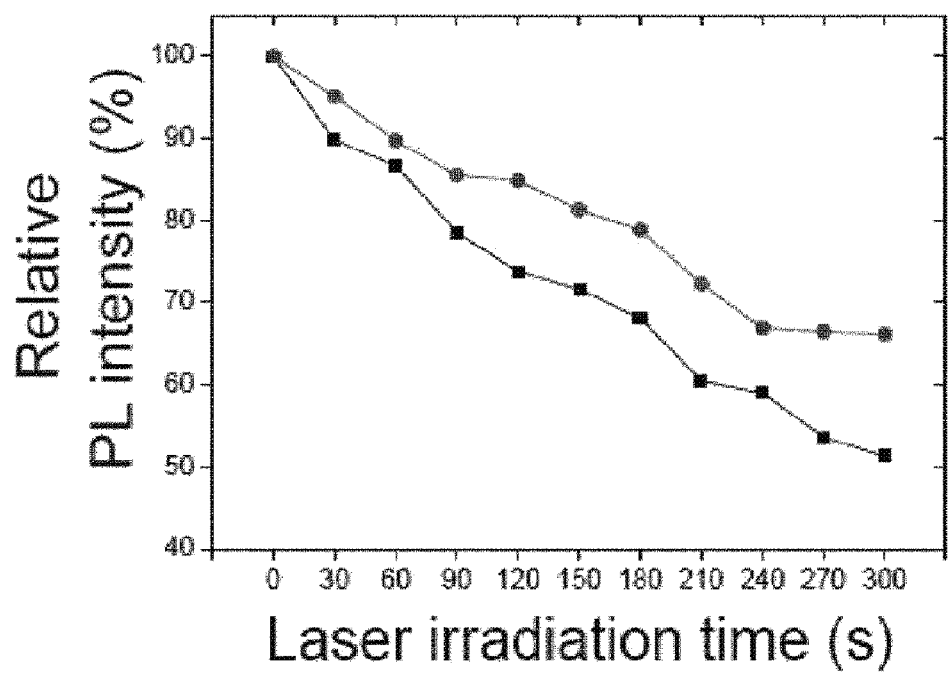
FIG. 9 is a graph showing the temporal fluorescence bleaching of free resorufin in water (black dot) and nanoABR (red dot) after reaction with H$_2$S in a PBS buffer, under laser irradiation at 532 nm for 5 minutes.

Specifically, based on the enhanced reactivity of nanoABR induced by SKC in a PBS buffer, its fluorogenic sensing characteristics were evaluated. As shown in the results on ABR in organic media, nanoABR also showed highly selective fluorescence reactivity to $H_2S$ among various biologically relevant reactive chemical species (FIG. 6). The nanoABR reacted with $H_2S$ showed evolution of absorption and fluorescence bands ($\lambda_{max.abs}$=575 nm, $\lambda_{max.fl}$=600 nm) that are typical of the monomer-like spectral profiles of resorufin (FIG. 7). However, these were all notably red-shifted compared to typical monomeric spectra of free resorufin in water ($\lambda_{max.abs}$=555 nm, $\lambda_{max.fl}$=585 nm), indicating that the negatively solvatochromic resorufin molecules recovered after the sensing reaction are kept in the less polar nanoreactor medium instead of released (FIG. 8). In addition, the recovered fluorescence of the nanoABR reacted with $H_2S$ is more photostable than free resorufin under laser irradiation at 532 nm (FIG. 9). As such, the improved photostability can be ascribed to the oxygen-shielding effect by nanoparticle encapsulation, thereby further confirming the retention of the recovered resorufin in the nanoreactor.

Figure 10:
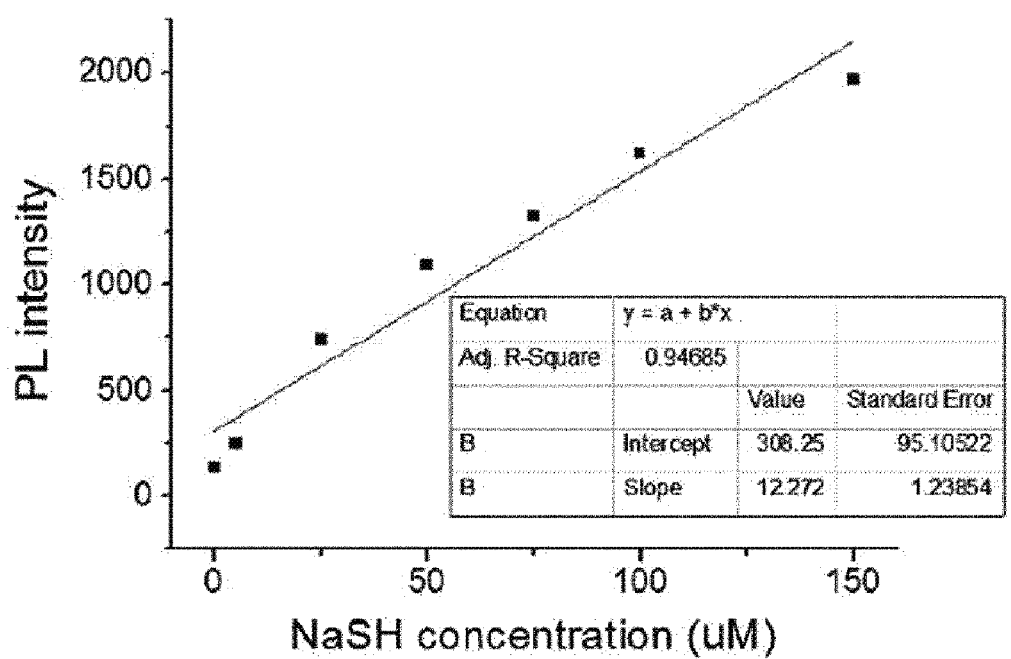
FIG. 10 is a graph showing the fluorescence intensity of nanoABR depending on the concentration of NaHS.
Figure 11:
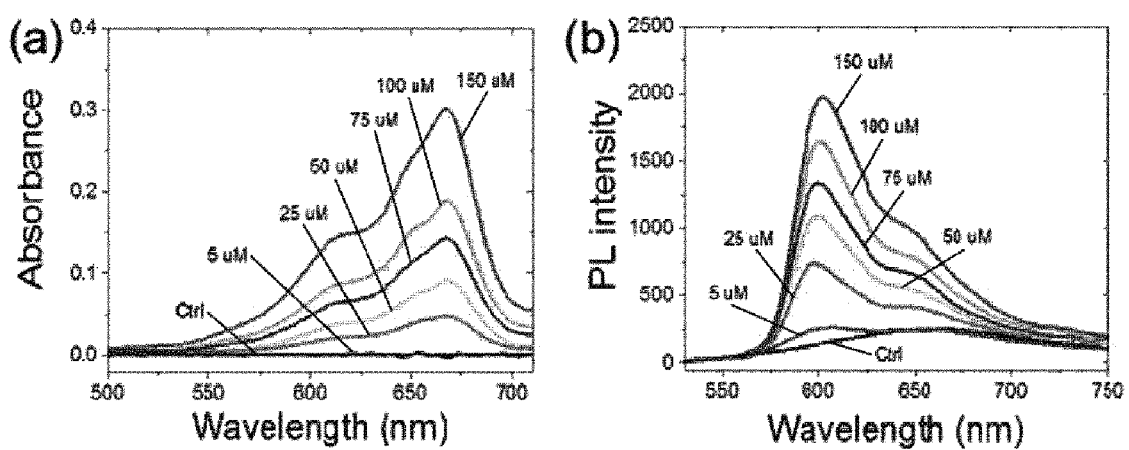
FIG. 11 is graphs showing the spectra of (a) the methylene blue absorption and (b) the nanoABR fluorescence (excited at 480 nm) in the presence of NaHS at various concentrations in PBS.

FIG. 4c shows the temporal evolution of fluorescence recovery when nanoABR was treated with NaHS (100 µM) in a PBS buffer. As shown by the curve fitting in FIG. 4d, the fluorescence intensity at 600 nm shows a mono-exponential rise profile with a kinetic rate ($k_r$) of $1.96 \times 10^{-3}$ $s^{-1}$. Although the completion of the reaction took about 60 minutes, the initial fluorescence reactivity was intense enough for the signal to be notably detected within 1 minute (the inset of FIG. 4c), and thus it can be applied to the real-time monitoring of $H_2S$ in biological systems. FIG. 4e shows the spectroscopic response depending on the concentration of NaHS in a PBS buffer, and the fluorogenic signal shows a linear correlation in the examined concentration range (5 µM to 150 µM). The detection limit of nanoABR was calculated to be 18 nM (FIG. 10), which is superior to the conventional colorimetric methylene blue formation assay (FIG. 11). Considering the physiological concentrations of $H_2S$ (serum: 30 µM to 100 µM, brain: 150 µM), the achieved detection sensitivity of nanoABR may allow for suitable monitoring of disease-related abnormal $H_2S$ levels in in vivo or in vitro biological samples.

Example 5: In Vitro Cell Labeling and Imaging

A human cervical epitheloid carcinoma (HeLa) cell line was maintained in DEAM with 10% FBS, L-glutamine ($5 \times 10^{-3}$ M), and gentamicin (5 µg $mL^{-1}$), in a humidified 5% $CO_2$ incubator at 37° C. The cells were seeded onto 35 mm culture dishes and allowed to grow until 70% confluence. Prior to the experiment, cells were washed twice with the PBS buffer (pH 7.4) and then incubated in serum-free medium (1.9 mL) containing a nanoABR dispersion solution (100 µL). For endogenous sulfide imaging, cells were pretreated for 30 minutes in a serum-free medium containing sodium nitroprusside (SNP, 100 µM). For an inhibition test, cells were pretreated with DL-propargylglycine (PAG, 100 µM) for 30 minutes. The pretreated cells were washed twice with the PBS buffer (pH 7.4) to remove free nanoparticles just before the data acquisition, and subjected to microscopic imaging with a LEICA DMI3000B microscope equipped with a Nuance FX multispectral imaging system (CRI, USA).

Figure 12:
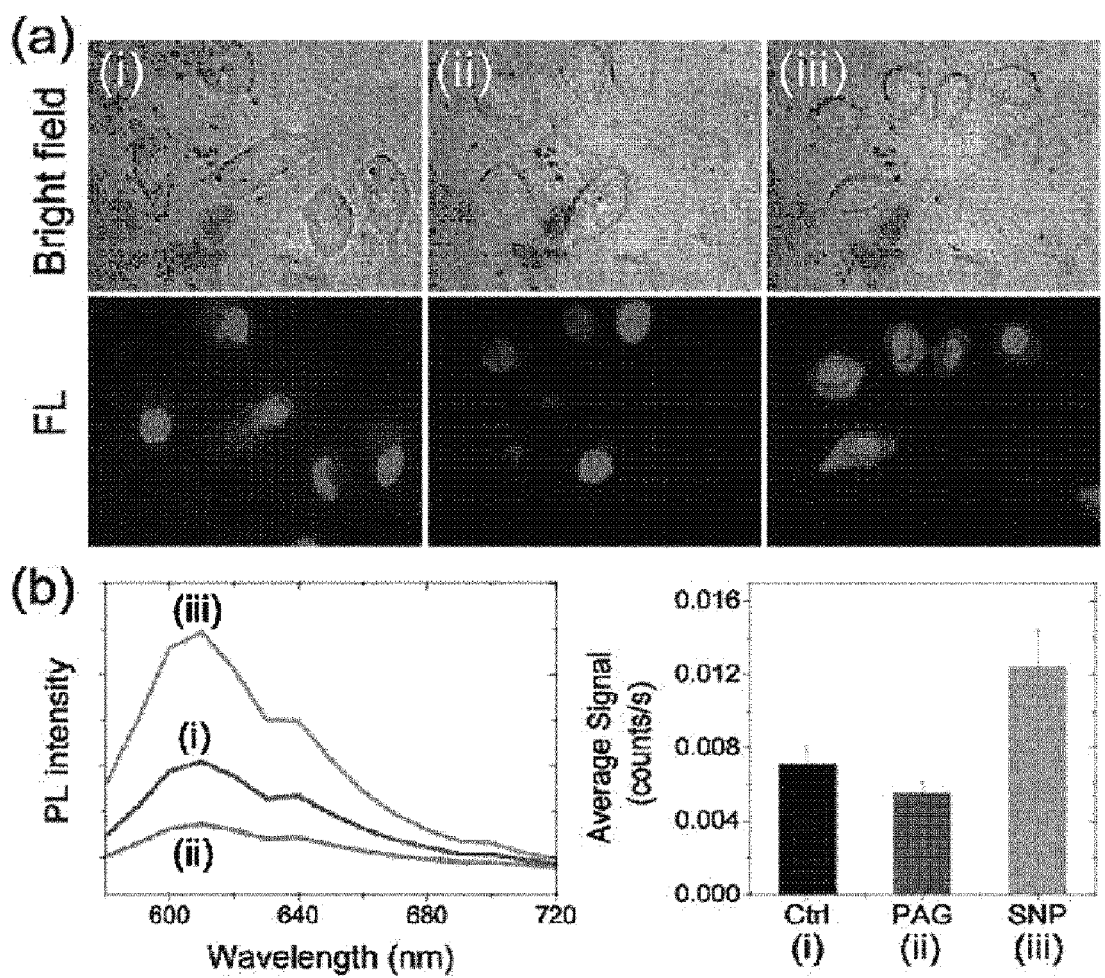
Figure 13:
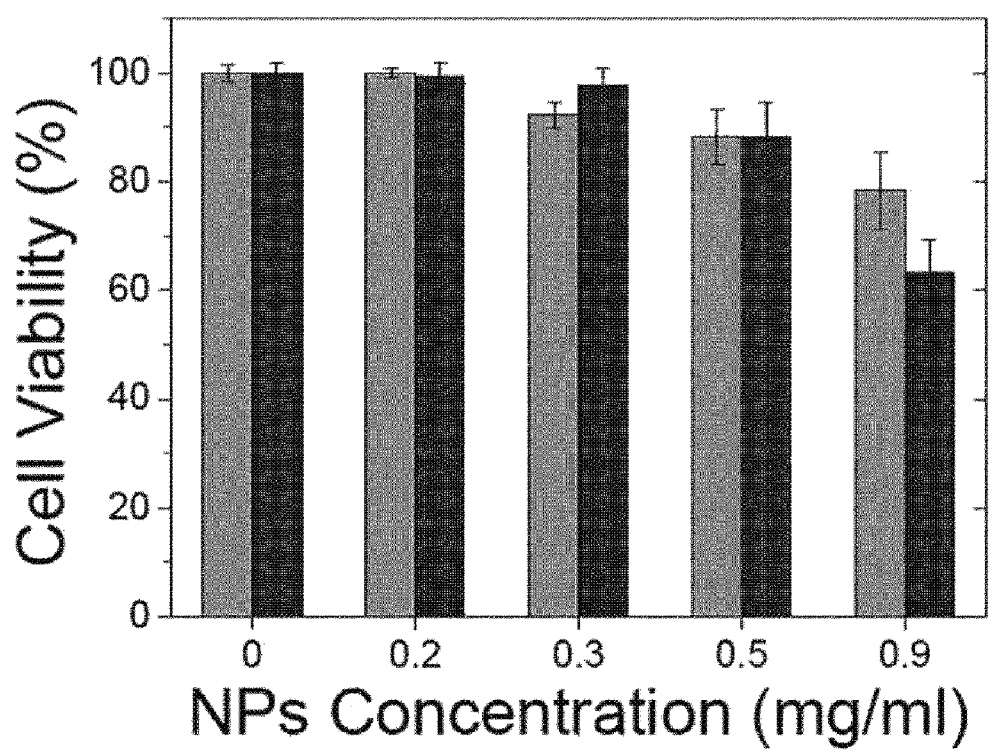
FIG. 13 is a graph showing the cytotoxicity of nanoABR against HeLa cells.

In order to demonstrate the feasibility of using nanoABR as a bioprobe, cellular internalization and fluorescence imaging of endogenous $H_2S$ by using HeLa cells were studied in the presence of chemical agents that stimulate or inhibit cellular generation of $H_2S$ (FIG. 12). When intact HeLa cells without chemical treatment were used as a control group, one-hour incubation with nanoABR at 37° C. was enough for reliable imaging of cytosolic fluorescence reactivity (FIG. 12a), suggesting that nanoABR is sufficiently taken up by cells, and also that its reactivity is sensitive enough to detect normal levels of endogenous $H_2S$ produced by intracellular enzymes under a physiological condition. In order to induce abnormal overproduction of $H_2S$, cells were pretreated with sodium nitroprusside (SNP) that can upregulate $H_2S$-producing enzymes, cystathionine β-synthase (CBS), and cystathionine γ-lyase (CSE) by NO. In such a cellular model overproducing $H_2S$, nanoABR exhibited a more vivid cytosolic fluorescence reactivity that is two-fold more intense than that from the SNP-untreated control cells, reflecting the increased level of endogenous $H_2S$. Upon pretreating cells with propargylglycine (PAG, 100 µM), a selective inhibitor of CBS and CSE, the cytosolic fluorescence reactivity of nanoABR became remarkably weak compared to that in PAG-untreated control cells, confirming that all of the imaged signals are in fact a response to cellular $H_2S$. The cytosolic fluorescence spectra from cells, which are in accordance with that of resorufin along with their intensities depending on the cellular conditions (FIG. 12b), demonstrate that fluorogenic reactivity of nanoABR is operative to sensitively detect the level changes of endogenous $H_2S$ implicated in the cellular processes. The cell viability assay shows minimal toxic effects on live cells under the conditions adopted for imaging experiments (FIG. 13), suggesting the potential of nanoABR for biosensing applications.

Example 6: In Vitro Diagnostic Imaging of Diabetes

The animal studies have been approved by the animal care and use committee of Korea Institute of Science and Technology, and all handling of mice was performed in accordance with the institutional regulations. A type 2 diabetes mouse model was prepared using CD-1 mice (male, 10 weeks of age, Orient Bio Inc., Korea) by anaesthetizing with intraperitoneal injection of 0.5% pentobarbital sodium (0.01 mL/g). Diabetes was induced by intraperitoneal injection of streptozotocin (STZ, 100 µL, 40 mg/mL in a PBS buffer), and the injection was repeated 4 times for 1 month. Mice with blood glucose levels between 250 mg/dL and 450 mg/dL were selected for the study. Mice were sacrificed and blood was collected heparinized capillary tubes. The capillary tubes were centrifuged, and the separated plasma was collected in microfuge tubes. Fluorescence imaging of $H_2S$ in plasma was carried out with an IVIS spectrum imaging system (Caliper, USA).

Figure 14:
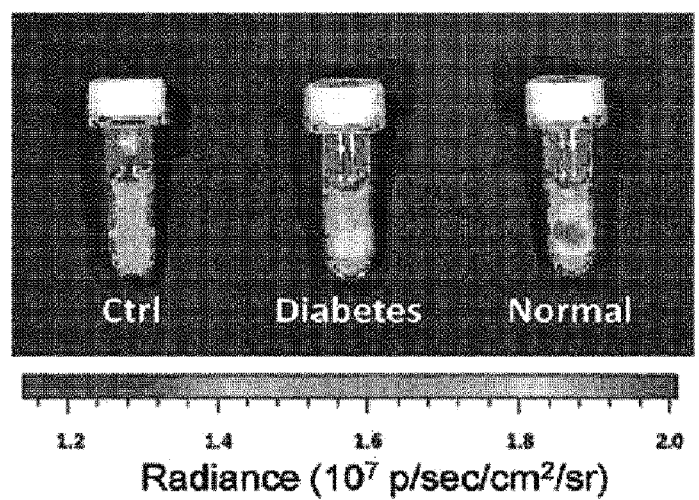
Figure 14:
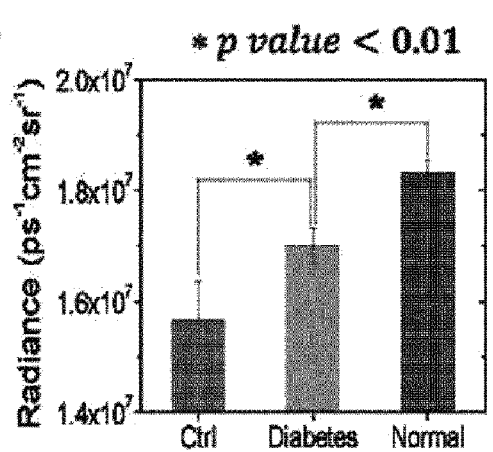
Figure 14:
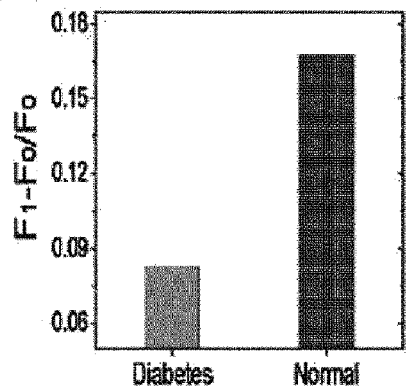
Figure 15:
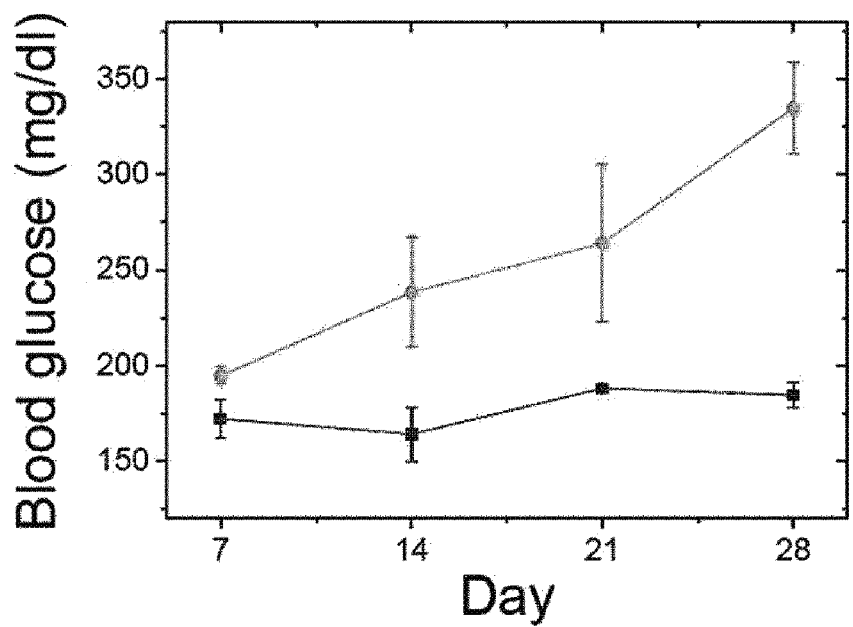
FIG. 15 is a graph showing the blood glucose levels of normal (blue) and diabetes (green) mouse models at selected time points after injection of streptozotocin (STZ) for inducing diabetes.

In order to evaluate the practical biomedical utility of nanoABR, the possibility of diagnosing diabetes in vitro by detecting the $H_2S$ level change in serum extracted from a mouse model with chemically induced type 2 diabetes was tested. The levels of $H_2S$ in diabetes patients are known to drop in blood but increase in organs such as the pancreas or liver, and thus can be used as a potential blood biomarker having clinical importance for in vitro diagnosis of diabetes. FIG. 14a shows the fluorescence reactivity of nanoABR to plasma $H_2S$, measured at 30 minutes after mixing with sera from normal or diabetic mice. It was observed that the fluorescence intensity recovered in sera collected from the diabetes model is statistically lower than that from normal mouse sera (FIG. 14b), suggesting a reduced blood concentration level of $H_2S$ due to diabetes. When normalized against the autofluorescence background from serum (FIG. 14c), this tendency is inversely correlated with an increase in the blood glucose level due to diabetes (FIG. 15). These results indicate that the molecularly assembled nanoABR probe retains structural integrity and high selectivity/sensitivity in biological fluids, and thus can suggest practical applicability for biomedical uses.

In conclusion, the present inventors prepared a novel self-immolative azidobenzyl-substituted resorufin-based $H_2S$-selective molecular probe (ABR) and studied its sensing reactivity within a molecularly assembled nanoreactor system (nanoABR) whose internal medium was elaborately engineered in terms of the electrical polarity on its surface. It was confirmed that the positively charged polar environment of the nanoABR interior established by co-assembly with a cationic co-surfactant (SKC) remarkably facilitates the nucleophilic sensing reaction of the embedded ABR in an electrostatic manner, through active recruitment of an anionic analyte (HS⁻) and stabilization of the anionic transition state of the sensing reaction. The sensing characteristics shown in physiological media having minimal cytotoxicity allowed for practical bioapplications to microscopic imaging of cellular processes and in vitro diagnostics of diabetes with blood samples from animal models.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A nanocomposite for detecting hydrogen sulfide ($H_2S$) comprising a $C_{10-25}$ alkane or haloalkane, a neutral first surfactant, a cationic second surfactant, and a reactive fluorophore, wherein:
   the nanocomposite is a self-assembly formed by co-assembly of the first surfactant and the second surfactant, in which the self-assembly comprises a hydrophobic core containing the $C_{10-25}$ alkane or haloalkane and the hydrophobic core comprises a reactive fluorophore, wherein
      the reactive fluorophore itself is non-fluorescent but exhibits fluorescence by a reaction with hydrogen sulfide, and
   wherein the $C_{10-25}$ alkane or haloalkane is 1-iodooctadecane.

2. The nanocomposite of claim 1, wherein the reactive fluorophore is a molecule that is cleaved by a reduction reaction with HS⁻ ions and decomposed into a fluorescent molecule and an aryl azide linker.

3. The nanocomposite of claim 1, wherein the reactive fluorophore is azidobenzylresorufin (ABR) in which a hydroxy (—OH) position, the $7^{th}$ position of resorufin, is substituted with azidobenzyl; or azidobenzylfluorescein in which a hydroxy (—OH) position, the $7^{th}$ position of fluorescein, is substituted with azidobenzyl.

4. The nanocomposite of claim 1, comprising the first surfactant and the second surfactant in a weight ratio of 10:90 to 50:50.

5. The nanocomposite of claim 1, comprising the reactive fluorophore in an amount of 1 to 30 parts by weight based on 100 parts by weight of the first surfactant.

6. The nanocomposite of claim 1, comprising the $C_{10-25}$ alkane or haloalkane in an amount of 20 wt % to 50 wt % based on the weight of the reactive fluorophore.

7. A method for preparing the nanocomposite of claim 1, comprising a first step of mixing a mixture of 1-iodooctadeance and a reactive fluorophore dissolved in an organic solvent with a mixed aqueous solution comprising a neutral first surfactant and a cationic second surfactant.

8. The method of claim 7, wherein the organic solvent is used in an amount of 0.2 vol % (v/v) to 5 vol % (v/v) relative to the aqueous solution.

9. The method of claim 7, wherein the nanocomposite is provided in the form of an aqueous dispersion solution.

10. A kit for detecting hydrogen sulfide comprising the nanocomposite of claim 1.

11. The kit of claim 10, wherein the kit is used for the diagnosis of a disease causing abnormal secretion of hydrogen sulfide, which is selected from the group consisting of chronic kidney disease, cirrhosis, Down's syndrome, Alzheimer's disease, and diabetes.

12. A method for providing information for the diagnosis of a disease causing abnormal secretion of hydrogen sulfide, comprising:
   a first step of contacting the nanocomposite of claim 1 with a specimen isolated from a subject suspected of having a disease;
   a second step of measuring a fluorescence spectrum of a sample obtained from the first step; and
   a third step of deriving the concentration of hydrogen sulfide in the specimen from the fluorescence spectrum obtained from the second step.

* * * * *